United States Patent [19]

Amoils

[11] Patent Number: 4,513,745
[45] Date of Patent: Apr. 30, 1985

[54] SURGICAL INSTRUMENTS AND METHODS PARTICULARLY ADAPTED FOR INTRA-OCULAR CUTTING AND THE LIKE

[76] Inventor: Selig P. Amoils, 4 Griswold Rd., Saxonwold, Johannesburg, South Africa

[21] Appl. No.: 204,782

[22] Filed: Nov. 7, 1980

Related U.S. Application Data

[63] Continuation of Ser. No. 917,454, Jun. 21, 1978, abandoned.

[51] Int. Cl.³ .............................................. A61B 17/32
[52] U.S. Cl. ...................................... 128/305; 604/22
[58] Field of Search .................. 128/305, 276, 334 R; 227/19, DIG. 1; 604/22

[56] References Cited

U.S. PATENT DOCUMENTS

| | | | |
|---|---|---|---|
| 3,388,847 | 6/1968 | Kasulin et al. | 227/19 |
| 3,701,352 | 10/1972 | Bosworth | 128/305 |
| 3,776,238 | 12/1973 | Peyman et al. | 128/305 |
| 3,815,604 | 6/1974 | O'Malley et al. | 128/305 |
| 3,884,238 | 5/1975 | O'Malley et al. | 128/305 |
| 3,994,297 | 11/1976 | Kopf | 128/305 X |

OTHER PUBLICATIONS

Peyman et al., "Experimental Vitrectomy", Arch Ophthal, vol. 86 (Nov. 1971) pp. 548–551.
Peyman et al., "Experimental Vitrectomy, New Technical Aspects", Amer. Jour. of Ophthal., vol. 75, No. 5, pp. 774–778.

*Primary Examiner*—Michael H. Thaler
*Attorney, Agent, or Firm*—Rines and Rines, Shapiro and Shapiro

[57] ABSTRACT

This disclosure involves an improved intra-ocular suction cutter or similar surgical instrument in which an annular reciprocating cutter chisel-cuts tissue against a terminal anvil with minimal traction and enables suction withdrawal of the severed tissue.

8 Claims, 4 Drawing Figures

SURGICAL INSTRUMENTS AND METHODS PARTICULARLY ADAPTED FOR INTRA-OCULAR CUTTING AND THE LIKE

This is a continuation application of Ser. No. 917,454, filed June 21, 1978, now abandoned.

The present invention relates to surgical instruments and methods and the like, being more particularly concerned with intra-ocular suction cutters for use in vitrectomy and lensectomy and the like.

Various types of intra-ocular and similar suction cutters have been evolved for these and other uses, such as instruments comprising an outer tube with an aperture near its tip and a closely fitting reciprocating inner tube having a sharp end near the tip of the outer tube; and wherein, in use, tissue is drawn into the aperture by suction and is severed by the inner tube by a cutting action against the edge of the aperture. Among such intra-ocular suction cutters, for example, is the Peyman Vitrophage and other cutters described and illustrated at pages 113 to 122 of the text book, "Advances in Uveal Surgery, Vitreous Surgery, and the Treatment of Endophthalmitis", by Peyman and Sanders, published by Appleton-Century-Crofts, Division of Prentice-Hall, Inc. in 1975 (ISBN 0-8385-0051-X). Among the disadvantage of such cutters is that sometimes, after the parts have become worn, or if the inner tube is not a very close-tolerance fit within the outer tube, the tissue is just not severed by the inner tube, and instead, without being cut, is pulled into the end of the outer tube. It is, however, essential to prevent such traction while cutting (cf "Principles of Instrumentation" by Stephen J. Ryan Jr.—Pars Plans Vitrectomy Symposium-Transactions: American Academy of Ophthalmology and Otolaryngology, May-June, 1976, Vol. 81, No. 3, page OP-352). The present invention is thus directed to the obviating not only of such traction rupture problems, but of the requirement of extremely close tolerance construction in manufacture and in subsequent operation, as well.

An object of the invention, accordingly, is to provide a new and improved intra-ocular suction cutter particularly useful for vitrectomy and lensectomy and that does not have such disadvantages, but, to the contrary, insures precise cutting and relaxes dimensional tolerance requirements.

A further object is to provide a novel surgical instrument and method for intra-ocular and similar applications wherein the features thereof are desired.

Other and further objects will be explained hereinafter and are more particularly delineated in the appended claims.

According to the invention, in summary, an anvil is provided in the outer tube near its tip, against which anvil the sharp end of the inner tube acts to cut tissue. The anvil is preferably located nearer the closed end of the tip than the aperture into which the tissue is drawn so as not to limit the area thereof through which the tissue is drawn. The anvil is preferably made of a soft material which is able to withstand the high temperature encountered in a sterilizing autoclave. Thus, while the material may be a hard plastic, such as a polytetrafluorethylene or the like, and possible detachably inserted for substituting anvils after some usage, it is preferably a metal or alloy, such as a noble metal or alloys as of sterling silver or gold.

The cross-section of the anvil is preferably greater than that of the inner tube so that the possibility of the inner tube entering a gap between the outer tube and the anvil is prevented or minimized.

Preferred embodiments of the invention will now be described, by way of example, with reference to the accompanying drawings in which.

Figure 1:
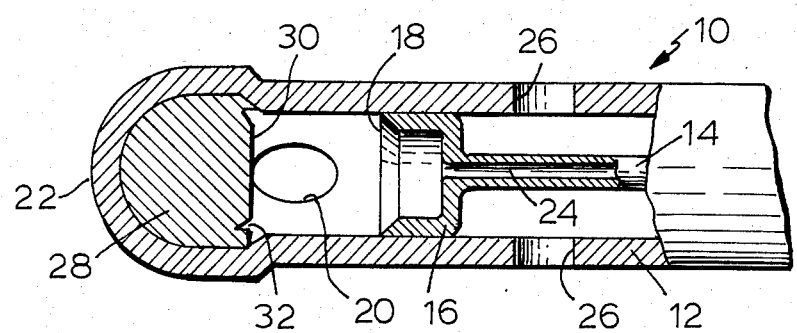
FIG. 1 is a partially sectioned diagrammatic side view through a vitreous infusion suction cutter of the invention.

Referring now to the drawings, there is shown part of the vitreous infusion suction cutter 10 of the invention, comprising an outer cylindrical hollow tubular member 12 within which is co-axially contained a narrow diameter inner tube 14. Both of the tubes may be of, for example, stainless steel. The free end of the inner tube 14, shown to the left, comprises a cup 16 which has a sharpened cutting annular periphery 18 and which is a sliding fit in close proximity to the inner wall of the outer tube 12.

An aperture or opening 20 is formed in the side of the outer tube 12 near its terminal tip 22, which is closed.

The hollow interior 24 of the inner tube 14 is connected, as is well-known, to a source of suction, not shown; while the other end of the inner tube 14 is connected to means for causing the inner tube 14 to reciprocate, such as any conventional solenoid and spring arrangement, also not shown so as not to detract from the novel constructional features of the invention as illustrated. Alternatively, pneumatic or other known means may be provided for this reciprocation purpose. Upstream of the maximum rearward (right-hand) position of the cup 16, the outer tube 12 has a pair of apertures 26 through which a saline or other suitable solution may be passed or flooded into the eye during the operation with the instrument.

Received within the end (left-hand) of the outer tube 12 downstream of the opening 20, is an anvil 28. This anvil 28, as before stated, may comprise sterling silver, gold or the like. The diameter or cross-section of the anvil 28 is preferably greater than that of the cup 16. The tip of the outer tube 12 is then slightly bulbous to accomodate the anvil 28.

As the inner tube 14 reciprocates to the end of its outward reciprocating movement, to the left, it strikes against the face 30 of the anvil 28 and, in due course, its annular cutter 18 forms a corresponding annular groove 32 therein. As the anvil 28 is of greater diameter or cross-section than the inner diameter of the free end of the outer tube 12 and hence the inner tube 14, the free end of the latter will always engage the face of the anvil and will not tend to open a gap between the anvil and side wall of the outer tube.

The enlarged diameter of the anvil 28 may be achieved, for example, by cooling a sterling silver slug or plug to a very low temprature, e.g. by means of liquid nitrogen, and heating the free end of the outer tube 12. The slug is then inserted into the free end of the tube which shrinks while the slug expands, distorting the tube. Alternatively, an oversized slug may be driven into the free end of the outer tube 12, the tip of which is then spun over to be closed.

If desired, as before mentioned, the tip containing the anvil 28 may be detachably secured, as by a threaded snap, bayonet or other connection, schematically illustrated at 30' in later described FIG. 4. This will enable the use of disposable anvils and cutters, as well.

The face 30 of the anvil 28 is preferably located as near as possible to the opening 20; and the opening 20 itself can be disposed extremely close to the tip 22.

In operational use, the end of the instrument is inserted into the eye so that the aperture or opening 20 is close to the tissue to be cut and so that the saline or other solution enters the eye cavity through the apertures 26. As the opening 20 is brought close to the affected tissue, vacuum suction is applied to the interior of the inner tube 14. The tissue is drawn into the opening 20 (all the foregoing steps being carried out in known manner). The reciprocating inner tube 14, as pneumatically, electrically or similarly driven, impacts the cutter 18 against the anvil face 30 at 32, effecting a cleanly severed impact cut. Thus it will be seen that the tissue is always impactcut with minimal or no traction. The severed tissue is then drawn up by suction through the inner tube for disposal.

Figure 2:
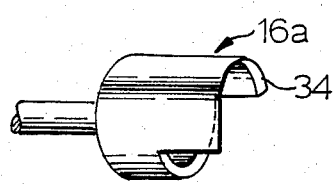
FIGS. 2 and 3 show modified details of a cutter and anvil, respectively, useful in the system of FIG. 1.

In a modification of the invention, as shown in FIG. 2, the cup 16a may have a part cut away. Thus the cup will have a cutting portion 34 adjacent the aperture or opening 20 only. In this embodiment, therefore, the interior of the outer tube will always be subject to suction.

Figure 3:
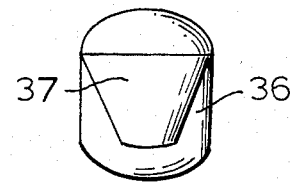

In another modification, as shown in FIG. 3, the anvil 36 may have a cut-away region or portion 37 remote from the opening so that the cutting cup 16 acts only on the striking face. This, too, reduces the area of contact between the cup periphery and the anvil face. Such an anvil 36 may be used with a cup 16 as shown in FIG. 1 or the cup 16a shown in FIG. 2.

Figure 4:
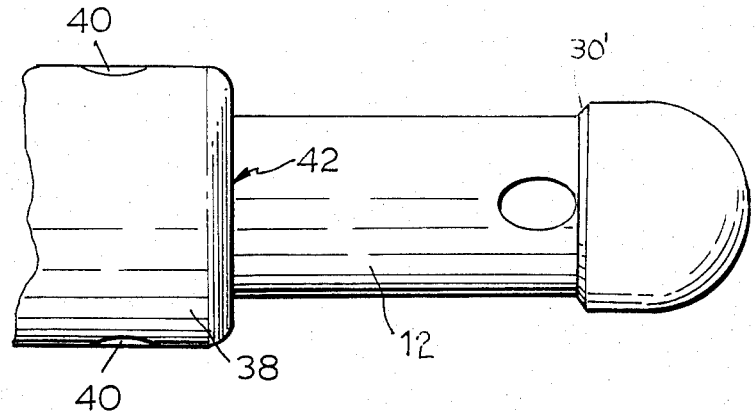
FIG. 4 is a simlar view of a modified cutter embodying features of the invention.

In a further modification, shown in FIG. 4, a surrounding tube 38 is provided about the outer tube 12. The surrounding tube 38 has apertures 40 near its end 42 which is sealed to the outer tube 12. The saline infusion liquid is, in use, passed down the annular space between the tubes 38 and 12 and is discharged into the eye. Thus there is no sealing problem bweteen the inner tube 14 to which suction is applied and the saline solution passage.

It will be noted that, in accordance with the constructional design of the invention, as the cutter and anvil wear in, the anvil recess will be molded to the shape of the cutter, thereby ensuring that the tissue is always impact-severed.

The invention is not limited to the precise constructional details hereinbefore described. By locating the anvil downstream from the aperture, the cup may cut tissue first by guillotining action in conjunction with the edge of the aperture as the annular cutting edge reciprocates closely past the same, and then by impact cutting action in which it, the tissue, is cut against the anvil as described above. Further, instead of sterling silver, the anvil may comprise a gold alloy. The number and location of infusion apertures may vary, and, if desired, moreover, the infusion facility may not be directly incorporated, but separate saline fluid supply may be provided.

The various modifications illustrated in the different figures may be incorporated in other figures of the drawing, also. Variations in configuration of the aspirating cutting part or aperture and of other parts as well may also be effected, and further modifications will also occur to those skilled in this art, such being considered to fall within the spirit and scope of the invention as defined in the appended claims.

What is claimed is:

1. In a surgical instrument for intra-ocular use, having in combination, a substantially cylindrical external hollow member, aperture means in said hollow member for receiving tissue-to-be-cut, annular cutting means disposed coaxially within the hollow member in close proximity to an inner wall thereof, the cutting means being adapted for reciprocatory motion within the hollow mmeber for effecting a guillotine cutting action on tissue drawn into said aperture means, and means cooperative with the cutting means for applying suction in the hollow member to draw the tissue-to-be-cut through the aperture means into the path of the reciprocating cutting means, the improvement comprising anvil means within said hollow member, the anvil means having an anvil surface adjacent said aperture means for cooperation with the cutting means to provide impact cutting of tissue drawn into said aperture means, the cutting means being adapted to effect said guillotine cutting action on tissue drawn into the aperture means prior to the impact cutting of the tissue against said anvil surface.

2. A surgical instrument as claimed in claim 1 and in which the said suction applying means comprises an inner hollow cylindrical element terminally connected to said annular cutting means to reciprocate the same as the element is coaxially moved back and forth within the said hollow member.

3. A surgical instrument as claimed in claim 1 and in which the said anvil surface is of cross-dimension slightly greater than that of the said annular cutting means.

4. A surgical instrument as claimed in claim 3 and in which the annular cutting means is of hard sharpened material such as stainless steel, and the anvil surface is of a softer material as of a noble metal and alloys of the same.

5. A surgical instrument as claimed in claim 1 and in which the said annular cutting means is part of a ring disposed adjacent the aperture means.

6. A surgical instrument as claimed in claim 1 and in which further aperture means is provided for flooding the tissue area outside the first-named aperture means with solution.

7. A surgical instrument as claimed in claim 1 and in which the said anvil surface is provided with a cut-away region external to the portion of such surface contacted by the cutting means.

8. A surgical instrument as claimed in claim 1 and in which said terminally provided anvil surface is detachably secured to said external member as for employing at least one of disposable anvil surfaces and cutting means.

* * * * *